US00PP16504P2

(12) United States Plant Patent
Hofmann

(10) Patent No.: US PP16,504 P2
(45) Date of Patent: May 2, 2006

(54) **NEW GUINEA *IMPATIENS* PLANT NAMED 'FISUPNIC HOTPINK'**

(50) Latin Name: *Impatiens hawkeri*
Varietal Denomination: Fisupnic Hotpink

(75) Inventor: Birgit C. Hofmann, Bendorf (DE)

(73) Assignee: Florfis AG, Binningen (CH)

( * ) Notice: Subject to any disclaimer, the term of this patent is extended or adjusted under 35 U.S.C. 154(b) by 102 days.

(21) Appl. No.: 10/829,215

(22) Filed: Apr. 22, 2004

(30) Foreign Application Priority Data

Apr. 22, 2003 (CH) ..... 03-1998

(51) Int. Cl.
*A01H 5/00* (2006.01)

(52) U.S. Cl. ..... Plt./318
(58) Field of Classification Search ..... Plt./318
See application file for complete search history.

*Primary Examiner*—Kent Bell
(74) *Attorney, Agent, or Firm*—Foley & Lardner LLP

(57) ABSTRACT

A new and distinct cultivar of New Guinea *Impatiens* plant named 'Fisupnic Hotpink' particularly characterized by the combined features of uniform, brilliant red-purple flower color; very large, round, flat flowers; uniform, deep green foliage; tall, v-shaped plant habit; mid season to moderately late flowering response; and good outdoor performance with good tolerance to both cold and heat.

1 Drawing Sheet

Genus and species of the plant claimed: *Impatiens hawkeri.*

Variety denomination: 'Fisupnic Hotpink'.

BACKGROUND OF THE INVENTION

The present invention comprises a new and distinct cultivar of New Guinea *Impatiens* plant, botanically known as *Impatiens hawkeri,* and hereinafter referred to by the cultivar name 'Fisupnic Hotpink'.

'Fisupnic Hotpink' is a product of a planned breeding program and originated from a hybridization made by the inventor, Birgit C. Hofmann, in a controlled breeding program in Hillscheid, Germany, in 1999.

The female parent was an unpatented proprietary seedling, designated no. 98-4128-1, which is characterized by very large, purple flowers, dark green foliage, and small to medium sized plant habit.

The male parent of 'Fisupnic Hotpink' was 'Fisupnic Lav' (U.S. Plant Pat. No. 13,224), having light violet flower color, dark green foliage, and vigorous growth habit.

'Fisupnic Hotpink' was discovered and selected as one flowering plant within the progeny of the stated cross by the inventor in April 2000 in a greenhouse in Galdar, Gran Canaria, Spain.

The first act of asexual reproduction of 'Fisupnic Hotpink' was accomplished when vegetative cuttings were taken from the initial selection in July 2000 in a controlled environment in Galdar, Gran Canaria, Spain, by, or under the supervision of the inventor.

Horticultural examination of plants grown from these cuttings initiated in the spring of 2001 in Hillscheid, Germany, and continuing thereafter, has demonstrated that the combination of characteristics as herein disclosed for 'Fisupnic Hotpink' are firmly fixed and are retained through successive generations of asexual reproduction. The new cultivar reproduces true to type.

'Fisupnic Hotpink' has not been observed under all possible environmental conditions. The phenotype may vary significantly with variations in environment such as temperature, light intensity and day length, without, however, any variation in genotype. The following observations, measurements, and comparisons describe plants grown in Hillscheid, Federal Republic of Germany, under greenhouse conditions which approximate those generally used in commercial practice.

BRIEF SUMMARY OF THE INVENTION

The following traits have been repeatedly observed and are determined to be basic characteristics of 'Fisupnic Hotpink', which in combination distinguish this *Impatiens* as a new and distinct cultivar:

1. uniform, brilliant red-purple flower color;
2. very large, round, flat flowers;
3. uniform, deep green foliage;
4. tall, v-shaped plant habit;
5. mid season to moderately late flowering response; and
6. good outdoor performance with good tolerance to both cold and heat.

Of the many commercial cultivars known to the inventor, the most similar in comparison to 'Fisupnic Hotpink' are the varieties 'Fisimp 112' (unpatented), 'Fisnics Hot Pink' (U.S. Plant Pat. No. 14,811), and 'Fisnics Hot Rose' (U.S. Plant Pat. No. 14,864).

In comparison to 'Fisimp 112', 'Fisupnic Hotpink' has somewhat taller, more upright and v-shaped plant habit, more evenly shaped flowers, and generally better outdoor performance.

In comparison to 'Fisnics Hot Pink', 'Fisupnic Hotpink' has a somewhat more reddish hue of flower color, lighter green foliage, and more vigorous growth habit.

In comparison to 'Fisnics Hot Rose', 'Fisupnic Hotpink' has somewhat larger flowers, uniform color, not variegated foliage, and taller plant habit.

BRIEF DESCRIPTION OF THE DRAWING

The accompanying photographic drawing shows typical flower and foliage characteristics of 'Fisupnic Hotpink' with colors being as true as possible with illustrations of this type. The photographic drawing shows a side view of a typical flowering plant of 'Fisupnic Hotpink'.

DETAILED BOTANICAL DESCRIPTION

In the following description color references are made to The Royal Horticultural Society Colour Chart (R.H.S.). The color values were determined indoors from plants growing in a greenhouse in May 2003, in Hillscheid, Germany.

The description is based on plants which were planted as rooted cuttings in 12 cm pots in late February 2003, and then grown in the greenhouse at a minimum temperature of 16° C. Most observations and measurements were made after the beginning of flowering in mid May, when the plants were about 12 weeks old.

Plant:

General appearance and form:

*Plant habit.*—Tall, round, bushy and very well branched, moderately dense; growth is indeterminate, though weak after beginning of flowering.

*Height.*—23.0 cm.

*Width.*—32.7 cm.

*Number of branches.*—16–18.

*Length of branches.*—16.0 cm.

*Internode length.*—5.0–7.0 cm.

*Diameter of branches.*—5–7 mm.

*Stem color.*—Brownish-red, RHS 182 A, partly green.

*Propagation.*—Terminal tips for cuttings.

*Rooting.*—Roots initiate in about 18 days at 22° C., from sticking to transplanting.

*Cultivation time.*—It takes about 10.5 weeks of growing time to produce a marketable flowering plant in a 12 cm pot.

Foliage:

*Leaf arrangement.*—Primarily in whorls.

*Shape of leaf.*—Elliptic, with acute base and acute to acuminate tip.

*Texture.*—Surface weakly glossy, smooth or faintly rugose. Margin: Slightly serrated, ciliated.

*Leaf length.*—12.0 cm.

*Leaf width.*—4.6 cm.

*Upper surface, main color.*—Medium green, uniform; mature leaves RHS 137 A, young leaves RHS 137 B to 137 C.

*Veins on upper surface color.*—Pale light green, RHS 145 C.

*Lower surface color.*—Light green, about RHS 138 B (both young and mature leaves).

*Veins on lower surface color.*—Brownish-pink, RHS 47 D.

*Petiole size.*—2.5–3.5 cm in length, 3 mm in diameter.

*Petiole color.*—Upper side RHS 181 C, lower side RHS 181 B.

Inflorescence:

*Flowering response.*—About 10 weeks after planting of rooted cuttings.

*Flowering season.*—Generally indeterminate, mainly from March to October, depending on light intensity.

Flower:

*Number of flowers per node.*—8–10, in various stages of development.

*Form of corolla.*—Single-type, 5 petals.

*Shape of corolla.*—Nearly round, nearly flat, with the petals well overlapping.

*Corolla size.*—Average length: 80 mm. Average width: 80 mm. Depth of corolla: 10 mm.

*Shape of petals.*—Cordate, only weakly lobed at the top end, base attenuate, Top petal: 35 mm long, 57 mm wide. Lateral petals: 36 mm long, 42 mm wide. Lower petals: 35 mm long, 49 mm wide. Texture: Smooth, velvety. Aspect: Mostly flat, possibly somewhat wavy.

*Color (general tonality from a distance of three meters).*—Bright red-purple, uniform.

*Color of upper surface.*—From RHS N57 B to N 66 B, no markings.

*Color of eye zone.*—From RHS N57 B to N 66 B.

*Color of lower surface.*—RHS 58 B to 58 C.

*Spur.*—Downwardly curved, 6.0 cm long, 3 mm in diameter at the flower end; color pink, RHS 53 D near the base.

*Peduncle color.*—Brownish-red, RHS 185 A.

*Peduncle length.*—Approximately 6.0 to 7.5 cm.

*Flower bud.*—Ovoid shape, 24 mm in length, 18 mm in width; color RHS 57 C to RHS 58 B.

Reproductive organs:

*Stamens.*—5 in number, fused, upper surface color is mainly RHS 52 A.

*Anthers.*—Fused, hooded.

*Pollen.*—Whitish-yellow, about RHS 8 D.

*Style and stigma.*—Five in number, very short, pale yellow, about RHS 150 D.

*Ovary.*—5-celled, 5 mm long, surface green, RHS 139 B.

Disease/pest resistance/susceptibility: No observations to date.

I claim:

1. A new and distinct cultivar of New Guinea *Impatiens* plant named 'Fisupnic Hotpink' as described and illustrated herein.

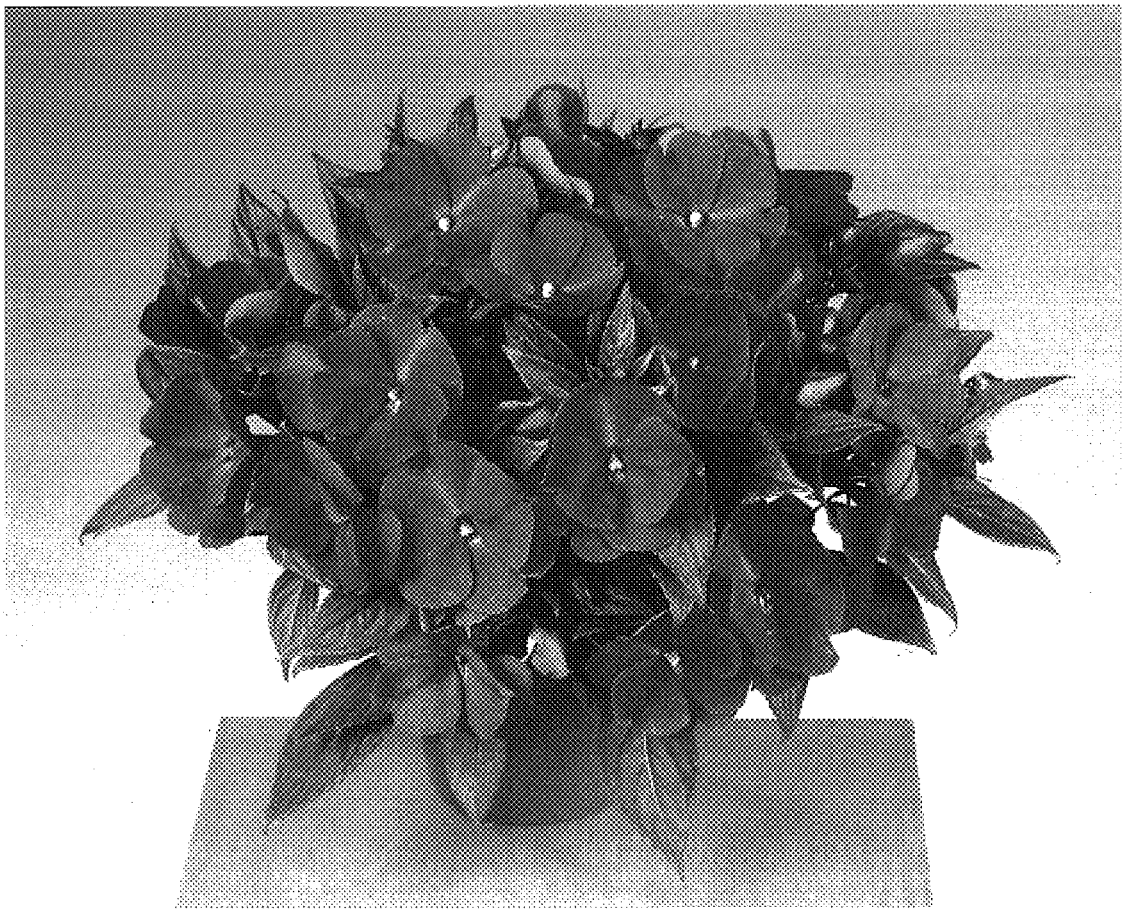

* * * * *